(12) United States Patent
Davies

(10) Patent No.: US 10,240,410 B1
(45) Date of Patent: Mar. 26, 2019

(54) HYDRAULIC FILTRATION AND PRESSURE TESTING DEVICE

(71) Applicant: Jason Davies, Houston, TX (US)

(72) Inventor: Jason Davies, Houston, TX (US)

(*) Notice: Subject to any disclaimer, the term of this patent is extended or adjusted under 35 U.S.C. 154(b) by 0 days.

(21) Appl. No.: 16/043,583

(22) Filed: Jul. 24, 2018

Related U.S. Application Data

(60) Provisional application No. 62/556,803, filed on Sep. 11, 2017.

(51) Int. Cl.
| | |
|---|---|
| *G01M 3/28* | (2006.01) |
| *G01N 1/14* | (2006.01) |
| *B08B 9/032* | (2006.01) |
| *B63B 35/44* | (2006.01) |
| *E21B 21/00* | (2006.01) |
| *E21B 21/06* | (2006.01) |
| *E21B 43/01* | (2006.01) |
| *E21B 47/10* | (2012.01) |
| *B01D 29/56* | (2006.01) |
| *E21B 49/08* | (2006.01) |
| *G01N 33/28* | (2006.01) |

(52) U.S. Cl.
CPC .......... *E21B 21/001* (2013.01); *B08B 9/0325* (2013.01); *B63B 35/44* (2013.01); *E21B 21/065* (2013.01); *E21B 43/0107* (2013.01); *E21B 47/1025* (2013.01); *G01M 3/2815* (2013.01); *B01D 29/56* (2013.01); *B01D 2201/202* (2013.01); *B01D 2201/265* (2013.01); *B01D 2221/04* (2013.01); *B01D 2221/08* (2013.01); *B63B 35/4413* (2013.01); *B63B 2035/448* (2013.01); *E21B 49/084* (2013.01); *G01N 1/14* (2013.01); *G01N 33/2823* (2013.01); *G01N 2001/1427* (2013.01); *Y10T 137/0424* (2015.04)

(58) Field of Classification Search
None
See application file for complete search history.

(56) References Cited

U.S. PATENT DOCUMENTS

| | | | |
|---|---|---|---|
| 4,337,829 A * | 7/1982 | Banzoli | E21B 33/0355 137/236.1 |
| 9,709,456 B1 * | 7/2017 | Clover | G01M 3/02 |
| 2003/0094419 A1 * | 5/2003 | Vickio, Jr. | B08B 9/0323 210/741 |

(Continued)

*Primary Examiner* — Daniel S Larkin
*Assistant Examiner* — David L Singer
(74) *Attorney, Agent, or Firm* — Wendy Buskop; Buskop Law Group, P.C.

(57) ABSTRACT

A floating vessel with a filtration and testing device integral thereon, for simultaneously performing cleaning of fluid used in the oil and natural gas industry for completions, workovers, and commissioning of wells while simultaneously pressure testing of two separate groups of pressurized equipment using fluid cleaned by the filtration and testing device. The floating vessel having a hull with a support structure mounted thereto which contains a cleaning cycle assembly and a pressure testing cycle assembly connected in parallel to a controller for cleaning fluid and regulating pressure by comparing fluid pressures to preset limits. The controller regulates cleaning of first and second dirty hydraulic fluids and regulates pressure of cleaned hydraulic fluids and secondary fluids for pressure testing of the two different groups of pressurized equipment simultaneously.

20 Claims, 7 Drawing Sheets

(56) References Cited

U.S. PATENT DOCUMENTS

| | | | | |
|---|---|---|---|---|
| 2005/0241677 | A1* | 11/2005 | Nealon | B08B 9/00 134/22.1 |
| 2009/0288836 | A1* | 11/2009 | Goodall | F16L 1/26 166/336 |
| 2016/0290889 | A1* | 10/2016 | Hilpert | E21B 33/06 |

* cited by examiner

HYDRAULIC FILTRATION AND PRESSURE TESTING DEVICE

CROSS REFERENCE TO RELATED APPLICATIONS

The present application claims priority to and the benefit of U.S. Provisional Patent Application Ser. No. 62/556,803 filed on Sep. 11, 2017, entitled "ONE PIECE FILTRATION AND TESTING DEVICE". This reference is hereby incorporated in its entirety.

FIELD

The present embodiment generally relates to a filtration and testing device for simultaneously pressure testing pressurized equipment while cleaning fluid used in oil and natural gas industry for completions, workovers, and commissioning of a well.

BACKGROUND

A need exists for a filtration and testing device for simultaneously cleaning fluid used in oil and natural gas industry for completions, workovers, and commissioning while providing pressure testing for pressurized equipment.

The present embodiments meet these needs.

BRIEF DESCRIPTION OF THE DRAWINGS

The detailed description will be better understood in conjunction with the accompanying drawings as follows.

Figure 1:
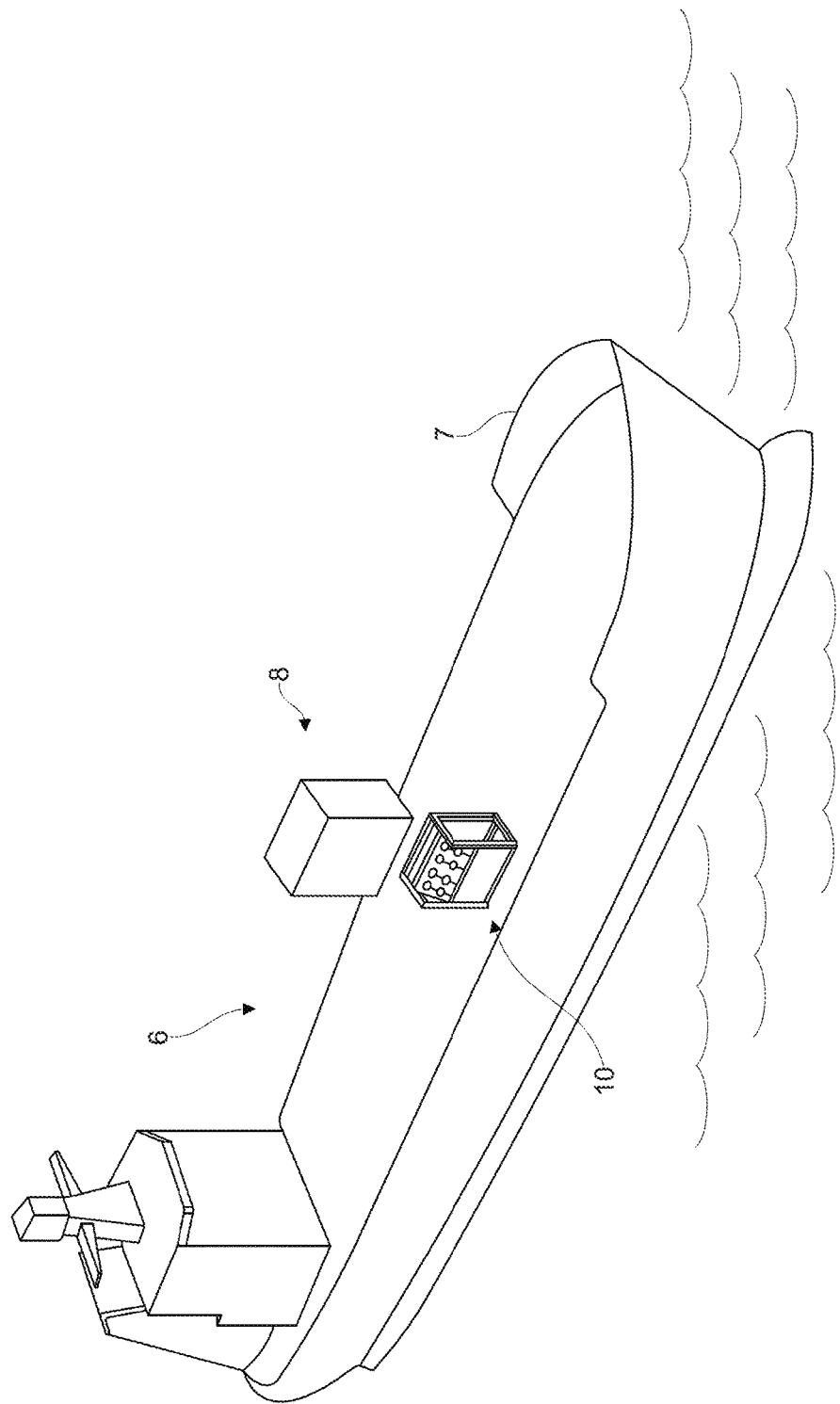
FIG. 1 depicts a floating ship having the filtration and testing device mounted thereto.

The present embodiments are detailed below with reference to the listed Figures.

DETAILED DESCRIPTION OF THE EMBODIMENTS

Before explaining the present floating vessel in detail, it is to be understood that the floating vessel is not limited to the particular embodiments and that it can be practiced or carried out in various ways.

Specific structural and functional details disclosed herein are not to be interpreted as limiting, but merely as a basis of the claims and as a representative basis for teaching persons having ordinary skill in the art to variously employ the present invention.

The invention relates to a floating vessel with integral a filtration and testing device for simultaneously performing (a) cleaning of fluid used in oil and natural gas industry for completions, workovers, and commissioning of a wells, (b) pressure testing of a first group of pressurized equipment using fluid cleaned by the filtration and testing device, and (c) pressure testing of a second group of pressurized equipment using fluid cleaned by the filtration and testing device.

The floating vessel has a hull with a support structure mounted to the hull.

The support structure houses a cleaning cycle assembly and a pressure testing cycle assembly.

The cleaning cycle assembly has a pump receiving low pressure air from a low pressure air supply. The low pressure air actuates the pump.

The actuated pump sequentially pulls: a first dirty hydraulic fluid from a first dirty hydraulic fluid supply; and a second dirty hydraulic fluid from a second dirty hydraulic fluid supply.

Next, in the cleaning cycle assembly has a multistage filtration device fluidly connected to the pump receiving the first or second dirty hydraulic fluid from the pump and producing a cleaned hydraulic fluid.

Fluidly connected to the cleaning cycle assembly is the pressure testing cycle assembly.

The pressure testing cycle assembly has a low pressure hydraulic fluid pump that simultaneously receives a low pressure air from the low pressure air supply and receives a cleaned hydraulic fluid from the cleaning cycle assembly. The low pressure hydraulic fluid pump transmits a low pressure cleaned hydraulic fluid.

The pressure testing cycle assembly has a high pressure hydraulic fluid pump that simultaneously receives a low pressure air from the low pressure air supply and receives a cleaned hydraulic fluid from the cleaning cycle assembly. The high pressure hydraulic fluid pump transmits high pressure cleaned hydraulic fluid.

The pressure testing cycle assembly has a low pressure fluid pump that simultaneously receives a low pressure air from the low pressure air supply and receives a secondary low pressure fluid from a secondary fluid supply. The low pressure fluid pump transmits a low pressure secondary fluid.

The pressure testing cycle assembly has a high pressure fluid pump that simultaneously receives a low pressure air from the low pressure air supply and receives a secondary high pressure fluid from the secondary fluid supply. The high pressure fluid pump transmits a high pressure secondary fluid.

The support structure houses a controller fluidly connected to each of the fluid pumps for regulating pressure of the low and high pressure cleaned hydraulic fluids and the low pressure and high pressure secondary fluids.

The controller has a low pressure cleaned hydraulic control section that compares to preset limits, the pressure of the low pressure air and low pressure cleaned hydraulic fluid.

The controller has a high pressure cleaned hydraulic control section that compares to preset limits, the pressure of the low pressure air and high pressure cleaned hydraulic fluid.

The controller has a low pressure secondary fluid control section that compares to preset limits, the pressure of the low pressure air and secondary low pressure fluid.

The controller has a high pressure secondary fluid control section that compares to preset limits, the pressure of the low pressure air and secondary high pressure fluid.

The floating vessel can utilize the controller to simultaneously (i) regulates the cleaning of the first and second dirty hydraulic fluids; (ii) regulates the flow of air and pressure of: high and low pressure cleaned hydraulic fluids for pressure testing of the first group of pressurized equipment, such as equipment on or next to the floating vessel, and (iii) regulates the flow of air and pressure of high and low pressure secondary fluids for pressure testing of the second group of pressurized equipment which can be on or next to the floating vessel.

A benefit of the invention is the floating vessel will prevent death of operators because the low pressure pumps are set to a max output pressure of 8,400 psi. All equipment is rated to 20,000 psi, which is over twice as high as the pressure being supplied for pressure being supplied by the low pressure pump when used onboard the vessel.

A benefit of the invention for the floating vessel is that the high pump pressure ratings are over twice the pump pressure being supplied reducing severe or fatal injuries. The high pressure pumps are set to a max output pressure of 25,000 psi. All equipment is rated to 60,000 psi, which is over twice as high as the pressure being supplied to the high pressure pump.

The floating vessel has the benefit that when used, the filtration and testing device provides a variety of safety mechanisms, individually regulated pumps with pressure relief valves and redundant burst discs for backup safety measures while operating to keep operators from dying while using the device.

The floating vessel provides a unit in a single hoist-able housing that has the ability to do pressure testing at a wide range of pressures, from very low hydraulic and fluid pressure, such as 10 psi to 6000 psi on the low pressure side and from 10 psi to 22.500 psi on the high pressure side simultaneously.

Another benefit of the floating vessel is that all of the pumps in the filtration and testing device are air regulated and can use ship's air to provide more options for pressure testing and flushing equipment enabling dual pressurized onboard equipment to be tested simultaneously.

The invention relates to a floating vessel with hull to which is mounted a filtration and testing device for simultaneously cleaning fluid used in oil and natural gas industry for completions, workovers, and commissioning of a well; while simultaneously pressure testing equipment using fluid cleaned by the device.

The floating vessel system has a cleaning cycle assembly with a diaphragm pump receiving: low pressure air from a low pressure air supply and receiving at least one of: a first dirty hydraulic fluid from a first dirty hydraulic fluid supply and a second dirty hydraulic fluid from a second dirty hydraulic fluid supply.

The floating vessel cleaning cycle assembly has a multi-stage filtration device that receives the dirty hydraulic fluid from the diaphragm pump and produces cleaned hydraulic fluid.

The floating vessel has a pressure testing cycle assembly having a controller that simultaneously controls and provides a low pressure hydraulic output, a high pressure hydraulic output, a low pressure secondary fluid output, and a high pressure secondary fluid output.

The floating vessel has a pressure testing cycle assembly that includes (a) a first liquid strainer straining the cleaned hydraulic fluid forming strained cleaned hydraulic fluid, (b) a second strainer straining low pressure air, and (c) a second liquid strainer straining a fluid from a fluid supply.

Four pumps are used, with pairs used in tandem, namely (i) a low pressure hydraulic fluid pump in tandem with (ii) a high pressure hydraulic fluid pump for presenting simultaneously both low pressure cleaned hydraulic fluid and high pressure cleaned hydraulic fluid to the controller; and (iii) a low pressure fluid pump presenting low pressure secondary fluid to the controller, with (iv) a high pressure fluid pump presenting high pressure secondary fluid to the controller.

The controller regulates the pressure of cleaned hydraulic fluid and pressure of another fluid to a low pressure hydraulic output, a high pressure hydraulic output, a low pressure fluid output, and a high pressure fluid output enabling pressure testing of pressurized equipment without electricity, while simultaneously cleaning hydraulic fluid or another fluid and flushing a chemical tote.

The following definitions are used herein:

The term "cleaning cycle assembly" refers to the filtration system having one or more spin on filters, sock filters and at least one pump such as a diaphragm pump. The cleaning cycle assembly can provide cleaning of dirty fluid at a rate such as 3 gallons per minute to 55 gallons per minute in embodiments. The particles removed by the cleaning cycle assembly can range in diameter from 12 micron to 0.5 micron.

The term "completions" as used herein refers, in petroleum production, the process of making a well ready for production (or injection). This principally involves preparing the bottom of the hole to the required specifications, running in the production tubing and it's associated down hole tools as well as perforating and stimulating as required. Sometimes, the process of running in and cementing the casing is also included. After a well has been drilled, should the drilling fluids be removed, the well would eventually close in upon itself. Casing ensures that this will not happen while also protecting the well stream from outside incumbents, like water or sand.

The term "commissioning" as used herein refers to the process of assuring that all systems and components of a building or industrial plant or large projects for which this statement can be made include chemical and petrochemical plants, oil and gas platforms and pipelines, are designed, installed, tested, operated, and maintained according to the operational requirements of the owner or final client. A commissioning process may be applied not only to new projects but also to existing units and systems subject to expansion, renovation or revamping.

The term "controller" refers to a mechanical device that is a flat, often vertical, area where control instrumentation are mounted to monitor and control machines or production lines and in places such as nuclear power plants, ships, aircraft floating vessels and mainframe computers. Older control panels are most often equipped with push buttons and analog instruments, whereas nowadays in many cases touchscreens are used for monitoring and control purposes. The controller performs regulating of the fluids by (i) comparing to preset limits the low pressure air and the low pressure cleaned hydraulic fluid pressure; (ii) comparing to preset limits the low pressure air and high pressure cleaned hydraulic fluid pressure; (iii) comparing to preset limits the low pressure air and first secondary low pressure fluid pressure; and (iv) comparing to preset limits the low pressure air and second secondary high pressure fluid pressure.

In embodiments, the controller simultaneously (i) regulates the pressure of cleaned hydraulic fluids for pressure testing of the first group of pressurized equipment 11a, (ii) regulates the pressure of secondary fluids for pressure testing of the second group of pressurized equipment 11b, (iii) regulates the cleaning of the first and second dirty hydraulic fluids and (iv) regulates flow of the first and second secondary high pressure fluid for use in that pressure testing The term "dirty hydraulic fluid" refers to any hydraulic fluid containing particulates, including hydraulic oils having a concentration, of particulate based on the total concentration of particulate in hydraulic fluid. National Aerospace Standards (NAS 1638), SAE AS4059 and ISO 4406 standards can be used to define the dirty hydraulic fluid that needs to be cleaned.

The term "dirty hydraulic fluid supply" refers to a reservoir, a tank, or flowing fluid from operations onboard the floating vessel, which can be a drill ship. In embodiments, a second dirty hydraulic fluid supply is unconnected and separate from the first dirty hydraulic fluid supply flowing from a reservoir, a tank, or fluid from operations onboard the floating vessel, which can be a drill ship. The first and second dirty hydraulic fluid supplies can be different hydraulic fluid supplies, from two completely separate sources. In an embodiment the first and second hydraulic fluid supply can be a recycle line. In yet another embodiment, the first and second hydraulic fluid supplies can be from the same source.

The term "filtration and testing device" refers to piece of equipment such as a Hydraulic Power Unit (HPU) used on a floating vessel in the oil and gas industry to perform pressure testing and flushing of Subsea equipment as well as cleaning and filtering hydraulic fluid.

The term "cleaned hydraulic fluid" refers to hydraulic fluid that has been cleaned by removing particles having a diameter, such as from 12 microns to 0.5 microns are removed from the hydraulic fluid, and/or contaminates such as unwanted oils are removed from the hydraulic fluid.

The term "floating vessel" refers to a displacement vessel with a hull, such as semisubmersible drilling rigs, a drill ship, a barge, a dynamic positioning floating platform with thrusters, a monohull floating ship, a catamaran floating vessel, a work boat, a support vessel to a drilling rig, a nautical term for all kinds of craft designed for transportation on water, such as ships, boats or submarines.

The term "fluid used in oil and natural gas industry for completions, workovers, and commissionings of wells" refers to hydraulic oil, such as OCEANIC™ 443, TRANSAQUA™ fluids or water.

The term "high pressure cleaned hydraulic fluid" refers to a hydraulic fluid with less than NAS or SAE class 6 micron diameter particulate, being driven to the controller by a high pressure pump.

The term "high pressure fluid pump" refers to a device for moving high pressure fluid (liquids or gases) by mechanical action with pressures such as ranging from 6000 psi to 30000 psi.

The term "high pressure hydraulic fluid pump" refers to a device for moving high pressure fluid (liquids or gases) by mechanical action such as pressures ranging from 5999 psi to 22500 psi. For example, a MAXIMATOR™ L150-2 pump made by MAXIMATOR™ is a good example of a usable high pressure hydraulic fluid pump. The pumps can be driven by air or noble gas at a pressure between 1 bar and 10 bar.

The term "high pressure fluid" refers to water or a hydraulic fluid that may or may not be cleaned to the NAS or SAE class 6 micron diameter particulate. The high pressure fluid is driven to the controller by a high pressure pump.

The term "hull" refers to the portion of the floating vessel for supporting the equipment including the deck, bow, stern, starboard and port sides.

The term "low pressure air supply" refers to a pressurized air supply, such as rig air, or air from compressors to tanks to run the pumps. The air pressure air in the low pressure air supply can range from 80 psi to 160 psi and all the numbers in between. The low pressure air supply provides a flow rate of 100 cubic feet per minute (cfm) to 190 cfm.

The term "low pressure cleaned hydraulic fluid" refers to a hydraulic fluid with less than NAS or SAE class 6 micron diameter particulate, being driven to the controller by a low pressure pump.

The term "a low pressure fluid" refers to a hydraulic fluid that may or may not be cleaned to the NAS or SAE class 6 micron diameter particulate. The low pressure fluid is driven to the controller by a low pressure pump. The low pressure fluid could be water.

The term "low pressure fluid pump" refers to a device for moving low pressure fluid (liquids or gases) by mechanical action such as pressures ranging from 5 psi to 5999 psi.

The term "low pressure hydraulic fluid pump" refers to a device for moving low pressure fluid (liquids or gases) by mechanical action such as pressures ranging from 5 psi to 6000 psi. For example, a MAXIMATOR™ GX 60 pump made by MAXIMATOR™ is a good example of a usable low pressure hydraulic fluid pump. The pumps can be driven by air or noble gas pressure between 1 bar and 10 bar.

The term "multistage filtration device" refers to a filtration system having one or more spin on filters, and at least one sock filter that clean dirty fluid sequentially using the pump in the cleaning cycle assembly to a rate of 5 gallons per minute to 50 gallons per minute to produce a cleaned hydraulic fluid.

The term "oil and natural gas industry" refers to the petroleum industry, also known as the oil industry or the oil patch, includes the global processes of exploration, extraction, refining, transporting (often by oil tankers and pipelines), and marketing of petroleum products. The largest volume products of the industry are fuel oil and gasoline (petrol). Petroleum (oil) is also the raw material for many chemical products, including pharmaceuticals, solvents, fertilizers, pesticides, synthetic fragrances, and plastics. The industry is usually divided into three major components: upstream, midstream, and downstream. Midstream operations are often included in the downstream category.

The term "pressurized equipment" refers to equipment such as tubing hangers, running tools, valves and bore for use in subsea Christmas trees and umbilicals, and workover packages. Pressurized equipment can be connectors, tree caps, hydraulic flying leads, steel flying leads, actuators, accumulators, jumpers and manifolds.

The term "pressure testing" refers to a non-destructive test performed to insure the integrity of pressurized equipment using low and high pressure pumps to see if the seals hold up to preset limits, such as 22,500 psi.

The term "pressure testing cycle assembly" refers to a portion of the filtration and testing device that performs the pressure testing on groups of pressurized equipment, including for example low pressure pumps with pressures ranging from 5 psi to 5999 psi and high pressure pumps reaching pressures ranging from 6000 psi to 30000 psi. The pressure testing cycle assembly is used for functioning valves, pressure testing Christmas trees and bore testing The term "pump" refers to a device that moves fluids using air in the cleaning cycle assembly from 5 gallons a minute to 50 gallons a minute, such as a diaphragm pump or another type of displacement pump.

The term "secondary fluid" refers to water, non-hydraulic oils, or hydraulic fluid the same or different from the dirty hydraulic fluid.

The term "support structure" refers to a skid, a frame, a housing, a trailer, a modular group of support members, forming a perforated device, such as a cage, connected together around the components of the filtration and testing device. The support structure forming protection around the components to prevent damage to the components, such as from force 3 Hurricane winds or impacts at 100 mph. In embodiments, the support structure can contain pad eyes for lifting by a crane so the entire unit can be repositioned on the floating vessel.

The term "workover packages" or "well intervention", is any operation carried out on an oil or gas well during, or at the end of, its productive life that alters the state of the well or well geometry, provides well diagnostics, or manages the production of the well. Subsea well intervention offers many challenges and requires much advance planning. The cost of subsea intervention has in the past inhibited the intervention but in the current climate is much more viable. These interventions are commonly executed from light/medium intervention vessels or mobile offshore drilling units (MODU) for the heavier interventions such as snubbing and workover drilling rigs.

The controller has no processor and requires no electricity.

In embodiments, the controller operates without the need for electricity and wherein the multistage filtration device flows cleaned hydraulic fluid to at least one of: a first dirty hydraulic fluid supply and a second dirty hydraulic fluid supply.

In embodiments, the low pressure air is strained prior to actuating each pump.

In embodiments, a first liquid strainer receives cleaned hydraulic fluid forming a strained cleaned hydraulic fluid; and a second strainer strains low pressure air and forms strained low pressure air.

In embodiments, a second liquid strainer strains a fluid from a fluid supply and forms strained fluid.

In embodiments, the low pressure hydraulic fluid pump receives strained cleaned hydraulic fluid and the high pressure hydraulic fluid pump receives strained hydraulic fluid.

In embodiments, a first ball valve regulates flow from the fluid supply, and a first air ball valve regulates flow of the low pressure air.

In embodiments, a third ball valve regulates flow of a first dirty hydraulic fluid, a fourth ball valve regulates flow of a second dirty hydraulic fluid, and a fifth ball valve regulates flow between the first and second dirty hydraulic fluids, a sixth ball valve regulates flow of cleaned hydraulic fluid to the low pressure hydraulic fluid pump and the high pressure hydraulic fluid pump and a seventh ball valve regulates flow of cleaned hydraulic fluid from the multistage filtration device.

In embodiments, a first air filter and a second air filter are connected in series for cleaning low pressure air respectively, from the low pressure air supply.

In embodiments, a plurality of fluid relief valves are used, each fluid relief valve is mounted inline from the low pressure fluid pump, and the high pressure fluid pump respectively, prior to the controller.

In embodiments, a plurality of burst discs are used, wherein each burst disc is mounted in line with the fluid relief valves, respectively.

In embodiments, a plurality of hydraulic relief valves are used, each hydraulic relief valve is mounted inline from the low pressure hydraulic fluid pump and the high pressure hydraulic fluid pump respectively, prior to the controller.

In embodiments, a plurality of hydraulic burst discs are used, wherein each hydraulic burst discs is mounted in line with the hydraulic relief valves, respectively.

In embodiments, the low pressure air supply transmits low pressure air at a pressure from 1 psi to 160 psi.

In embodiments, the multistage filtration device includes a 1 to 3 micron spin on filter receiving the first or second dirty hydraulic fluid and forming slightly cleaned hydraulic fluid; a 0.5 to 3 micron spin on filter fluidly connected to the 1 to 3 micron spin on filter forming a partially cleaned hydraulic fluid from the slightly cleaned hydraulic fluid; 0.5 to 10 micron sock filter fluidly connected to the 0.5 to 3 micron filter forming the cleaned hydraulic fluid from the partially cleaned hydraulic fluid; and a sample port connected to a tubing from the pump enabling authentication of filtration of the hydraulic fluid.

In embodiments, a fluid vent port is connected to the low pressure secondary fluid control section and high pressure secondary fluid control section of the controller; and a hydraulic vent port is connected to the low pressure hydraulic control section and the high pressure hydraulic control section of the controller.

In embodiments, a stand-alone 0.5 to 10 sock filter is used to receive at least one return fluid from each group of pressurized equipment.

In embodiments, the low pressure hydraulic control section has a first air regulator connected to the low pressure air supply; a first air ball valve controlling flow of low pressurize air to the low pressure hydraulic fluid pump; a first low pressure isolation valve controlling flow of low pressure hydraulic fluid; a low pressure hydraulic gauge measuring low pressure hydraulic fluid flowing from the low pressure hydraulic fluid pump; a low pressure hydraulic vent connected to a hydraulic vent port; and a hydraulic cross over valve connecting the low pressure hydraulic control section 30 to the high pressure hydraulic control section.

In embodiments, the high pressure hydraulic control section, and a second air regulator connected to the low pressure air supply; a second air ball valve fluidly controlling flow of low pressurize air to the high pressure hydraulic fluid pump; a first high pressure isolation valve controlling flow of high pressure hydraulic fluid; a high pressure hydraulic gauge measuring high pressure hydraulic fluid flowing from the high pressure hydraulic fluid pump; and a high pressure hydraulic vent connected to a hydraulic vent port.

In embodiments, the low pressure secondary fluid control section has a third air regulator connected to the low pressure air supply; a third air ball valve controlling flow of low pressurize air to the low pressure fluid pump; a second low pressure isolation valve controlling flow of low pressure secondary fluid; a low pressure fluid gauge measuring low pressure secondary fluid flowing from the low pressure fluid pump; a low pressure fluid vent connected to a fluid vent port; and a fluid cross over valve connecting the low pressure secondary fluid control section to the high pressure secondary fluid control section.

In embodiments, the high pressure secondary fluid control section has: a fourth air regulator connected to the low pressure air supply; a fourth air ball valve controlling flow of low pressurize air to the high pressure fluid pump; a second high pressure isolation valve controlling flow of high pressure secondary fluid; a high pressure fluid gauge measuring high pressure secondary fluid flowing from the high pressure fluid pump; and a high pressure fluid vent connected to a fluid vent port.

Turning now to the Figures, FIG. 1 depicts a floating ship 6 having the filtration and testing device mounted thereto.

FIG. 1 specifically portrays a floating vessel 6 having a hull 7 and a filtration and testing device 10 with a support structure 8 mounted in the hull 7.

The filtration and testing device 10 simultaneously performs (a) cleaning of fluid used in oil and natural gas industry for completions, workovers, and commissionings of a well, (b) pressure testing of a first group of pressurized equipment using fluid cleaned by the filtration and testing device, and (c) pressure testing of a second group of pressurized equipment using fluid cleaned by the filtration and testing device.

Figure 2A:
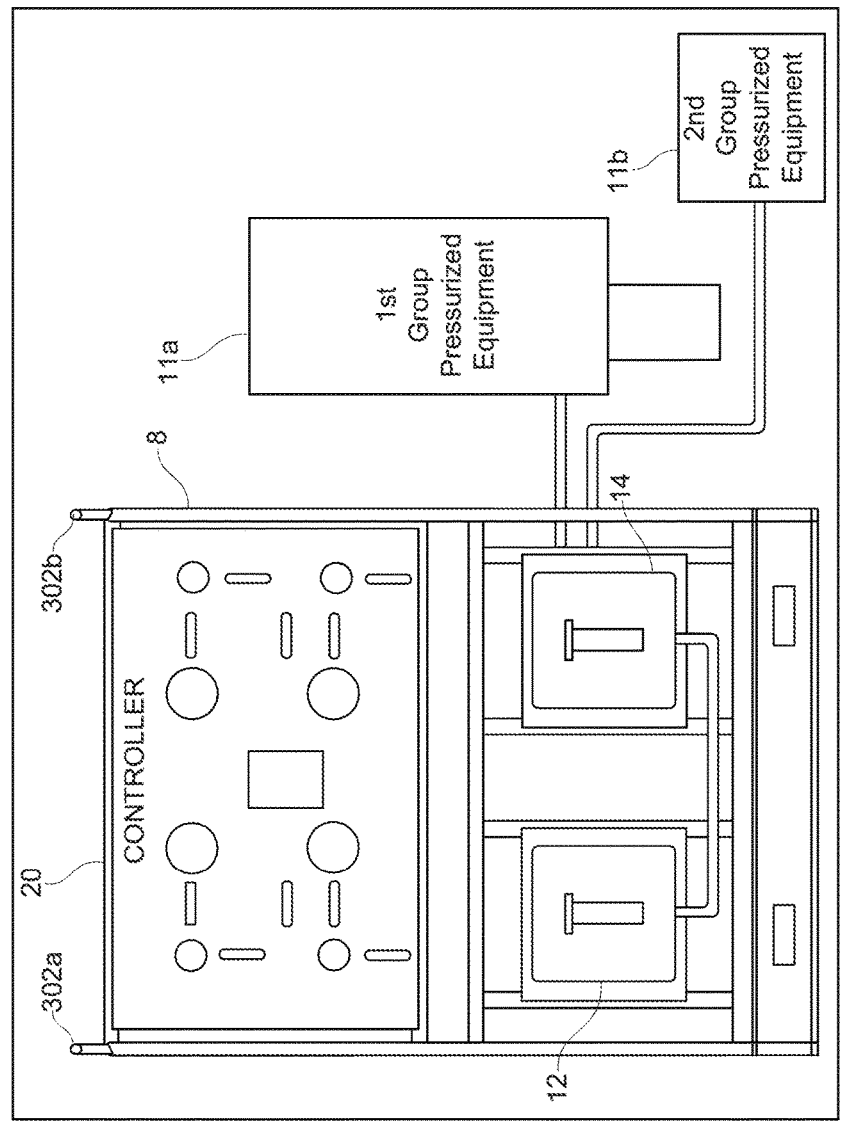
FIGS. 2A and 2B depict components of the filtration and testing device for simultaneously cleaning fluid used in oil and natural gas industry for completions, workovers, and commissioning providing pressure testing for pressurized equipment.
Figure 2B:
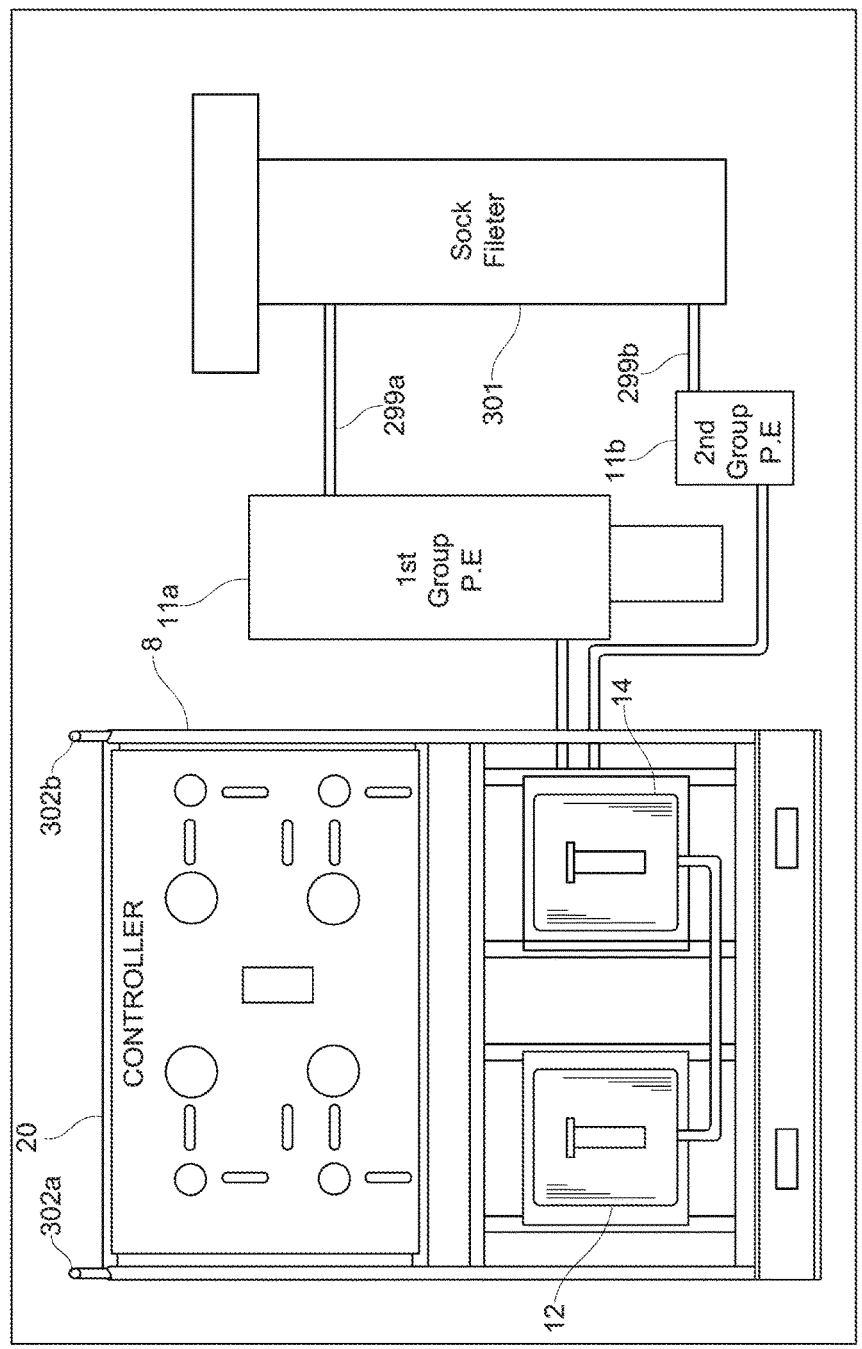

FIG. 2A-2B depict a support structure 8, which contains the filtration and testing device 10 shown in FIG. 1 for cleaning fluid used in oil and natural gas industry for completions, workovers, and commissionings of a well; while simultaneously providing pressure testing for two different groups of pressurized equipment 11a and 11b using the cleaned fluid.

Pad eyes 302a and 302b on the support structure 8 enable the filtration and testing device to be hoisted as a unit.

The support structure 8 contains the controller 20 that operates the cleaning cycle assembly 12 and the pressure testing cycle assembly 14.

In embodiments, the filtration and testing device contained by the support structure 8 can be connected to a first group of pressurized equipment 11a and a second group of pressurized equipment 11b. Each group of pressurized equipment can connect with a conduit to a stand-alone 0.5 to 10 micron sock filter 301 that is receiving return fluids 299a and 299b from the two groups of pressurized equipment 11a and 11b.

As an example, the support structure can be a 4 foot by 4 foot square skid made of 2" steel tubing, 2" or 3" angle iron, 6" steel 1-beams all certified welded and pull tested.

The support structure can be a cage, or a solid panel structure.

FIG. 2A depicts the support structure 8 without the stand-alone 0.5 to 10 micron sock filter 301 that is receiving return fluids 299a and 299b from the two groups of pressurized equipment 11a and 11b.

Figure 3:
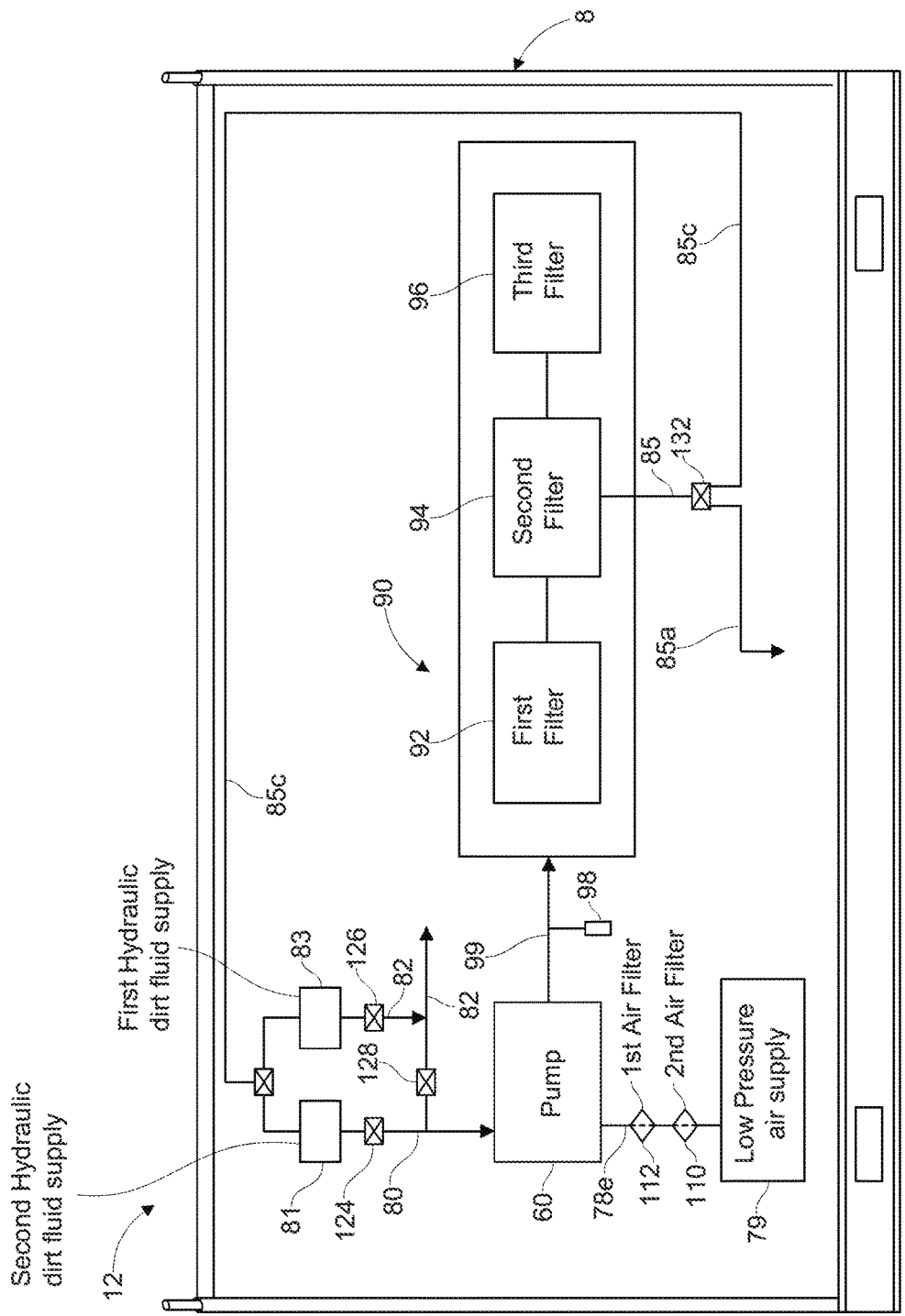
FIG. 3 depicts a cleaning cycle assembly of the filtration and testing device.

FIG. 3 shows an embodiment of the cleaning cycle assembly 12 within the support structure 8.

The cleaning cycle assembly 12 has a pump 60, such as a diaphragm pump, configured for receiving not only low pressure air 78 from a low pressure air supply 79 but simultaneously receiving at least one of: a first dirty hydraulic fluid 80 from a first dirty hydraulic fluid supply 81 and a second dirty hydraulic fluid 82 from a second dirty hydraulic fluid supply 83.

The cleaning cycle assembly 12 has a multistage filtration device 90 configured for receiving the dirty hydraulic fluid from the pump 60 and producing a cleaned hydraulic fluid 85.

The multistage filtration device 90 can have a first filter 92 that is a one micron to three micron spin on filter for initially receiving the dirty hydraulic fluid.

Connected to the spin on filter is a second filter 94 that is from 0.5 micron to 3 micron spin on filter.

Connected to the second spin on filter is a third filter 96 that is from 0.5 micron to 10 micron sock filter. The sock filter is connected in series with the second spin on filter 94.

A first air filter 110 can be connected in series with a second air filter 112 for cleaning low pressure air 78e as the low pressure air flows from the low pressure air supply 79. The air filters can remove water and particulate with a diameter in the range from 1 to 5 microns.

In embodiments, three ball valves control flow into the pump 60 of the cleaning assembly.

Multiple ball valves are used in the invention, but in the cleaning assembly, 3 are used. One of the ball valves of the cleaning assembly is termed "a third ball valve 124". The third ball valve 124 is used for regulating the first dirty hydraulic fluid 80 to the pump 60.

Another of the three ball valves in the cleaning assembly is referred to herein as "a fourth ball valve 126". The fourth ball valve 126 is used for regulating a second dirty hydraulic fluid 82.

The third ball valve of the three ball valves of the cleaning assembly is referred to herein as "a fifth ball valve 128." The fifth ball valve 128 is for regulating a cross over between the first and second dirty hydraulic fluids.

In embodiments, a seventh ball valve 132 regulates cleaned hydraulic fluid 85a to the high pressure hydraulic fluid pump. Cleaned hydraulic fluid 85c flows to increase circulation through the first or second dirty fluid supply.

A sample port 98 is installed on a tubing 99 from the pump 60 to the multistage filtration device 90.

This embodiment shows a support structure 8 supporting all the components forming a unit.

Figure 4A:
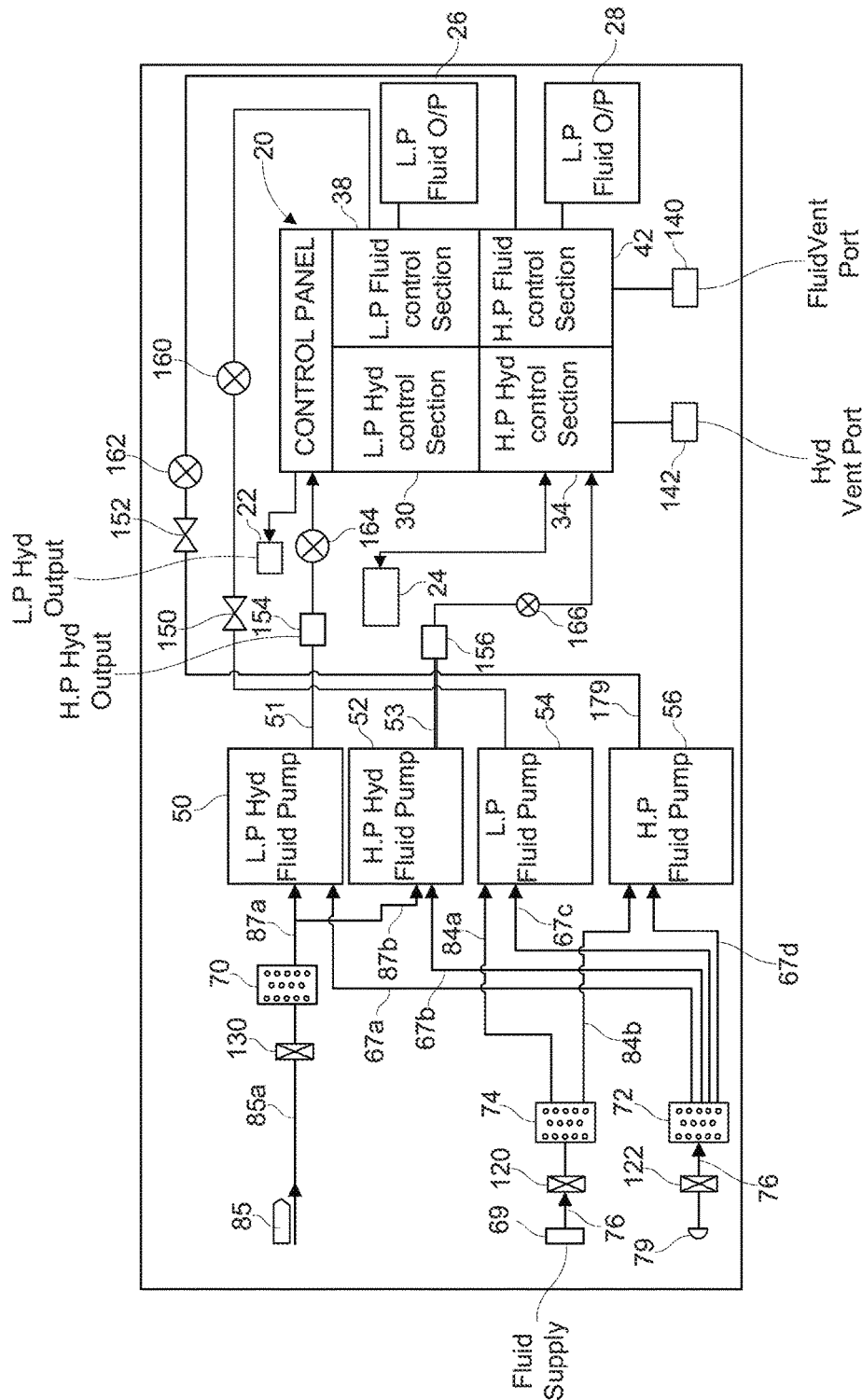
FIGS. 4A and 4B depict a pressure testing cycle assembly of the filtration and testing device.

FIG. 4A shows a pressure testing cycle assembly 14 capable of pressure testing two different groups of pressurized equipment simultaneously and contained within the same support structure as the cleaning assembly and the controller.

The pressure testing cycle assembly includes a controller 20.

The controller 20 provides simultaneously: a low pressure hydraulic output 22; a high pressure hydraulic output 24; a low pressure fluid output 26; and a high pressure fluid output 28.

The fluids can be water or another hydraulic fluid.

The controller 20 includes: a low pressure hydraulic control section 30; a high pressure hydraulic control section 34; a low pressure fluid control section 38; and a high pressure fluid control section 42, each control section controls fluid to an output.

In this embodiment, the pressure testing cycle assembly 14 includes a first liquid strainer 70 straining the cleaned hydraulic fluid 85 after the cleaned fluid flows through a ball valve 130, (termed herein "second ball valve") forming strained cleaned hydraulic fluids 87a and 87b.

In this embodiment, the pressure testing cycle assembly 14 includes a second strainer 72 straining low pressure air 78 from the low pressure air supply 79 after the low pressure air 78 passes through a ball valve 122 (referred to herein "first air ball valve 122") forming a plurality of strained low pressure air 67a, 67b, 67c and 67d.

In this embodiment, the pressure testing cycle assembly 14 includes a second liquid strainer 74 for straining fluid 76 from a fluid supply 69 after the fluid passes through a ball valve 120 (referred to herein a first ball valve 120) forming both strained fluid 84a that flows to low pressure fluid pump 54 and strained fluid 84b that flows to high pressure fluid pump 56.

For this embodiment, the pressure testing cycle assembly 14 includes: a low pressure hydraulic fluid pump 50 receiving strained cleaned hydraulic fluid 87a and strained low pressure air 67a and pumping low pressure cleaned hydraulic fluid 51 to the controller 20.

The pressure testing cycle assembly 14 includes: a high pressure hydraulic fluid pump 52 receiving strained cleaned hydraulic fluid 87b and strained low pressure air 67b and pumping high pressure cleaned hydraulic fluid 53 to the controller.

The pressure testing cycle assembly 14 includes: a low pressure fluid pump 54 receiving strained secondary fluid 84a from the second liquid strainer 74 and strained pressured air 67c from the second strainer 72 and pumping low pressure secondary fluid 77 to the controller 20.

The pressure testing cycle assembly 14 includes: a high pressure fluid pump 56 receiving strained secondary fluid 84b from the second liquid strainer 74 and strained low pressure air 67d from the second strainer 72 providing high pressure secondary fluid 179 to the controller 20.

The controller 20 regulates the pressure of cleaned hydraulic fluid to a low pressure hydraulic output 22 and a high pressure hydraulic output 24.

The controller 20 regulates the pressure of strained fluid to a low pressure fluid output 26 and a high pressure fluid output 28 enabling pressure testing of a pressurized equipment.

The filtration and testing device has a first ball valve 120 regulating the secondary fluid supply 69, such as a water supply, and a first air ball valve 122 regulating the low pressure air flow.

The filtration and testing device in embodiments can use a sixth ball valve 130 regulating cleaned hydraulic fluid 85 to the low pressure hydraulic fluid pump 50 and high pressure hydraulic fluid pump 52.

In embodiments, a fluid vent port 140 is connected to the controller and a hydraulic vent port 142 is connected to the controller with the two ports connected in parallel.

The pressure testing cycle assembly 14 is depicted a plurality of fluid relief valves 150 and 152.

In embodiments, one of the fluid relief valves is mounted inline from the low pressure fluid pump 54 and one of the fluid relief valves is mounted inline from the high pressure fluid pump 56 prior to fluid flowing to the controller.

The pressure testing cycle assembly 14 has a plurality of burst discs 160 and 162. One of the burst discs is mounted in series and in line with one of the fluid relief valves 150 and 152 respectively.

In embodiments, the pressure testing cycle assembly 14 has a plurality of hydraulic relief valves 154 and 156.

One of the hydraulic relief valves 154 is mounted inline from the low pressure hydraulic fluid pump 50 and one of the hydraulic relief valves 156 is mounted inline from the high pressure hydraulic fluid pump 52 prior to the controller 20.

A plurality of hydraulic burst discs 164 and 166 can be used. One of the burst discs is mounted in series and in line with one of the hydraulic relief valves 154 and 156 respectively.

One of the hydraulic burst discs can be mounted in conjunction with one of the hydraulic relief valves.

In embodiments, one of the hydraulic burst discs is mounted in series and in line with one of the hydraulic relief valves.

Figure 4B:
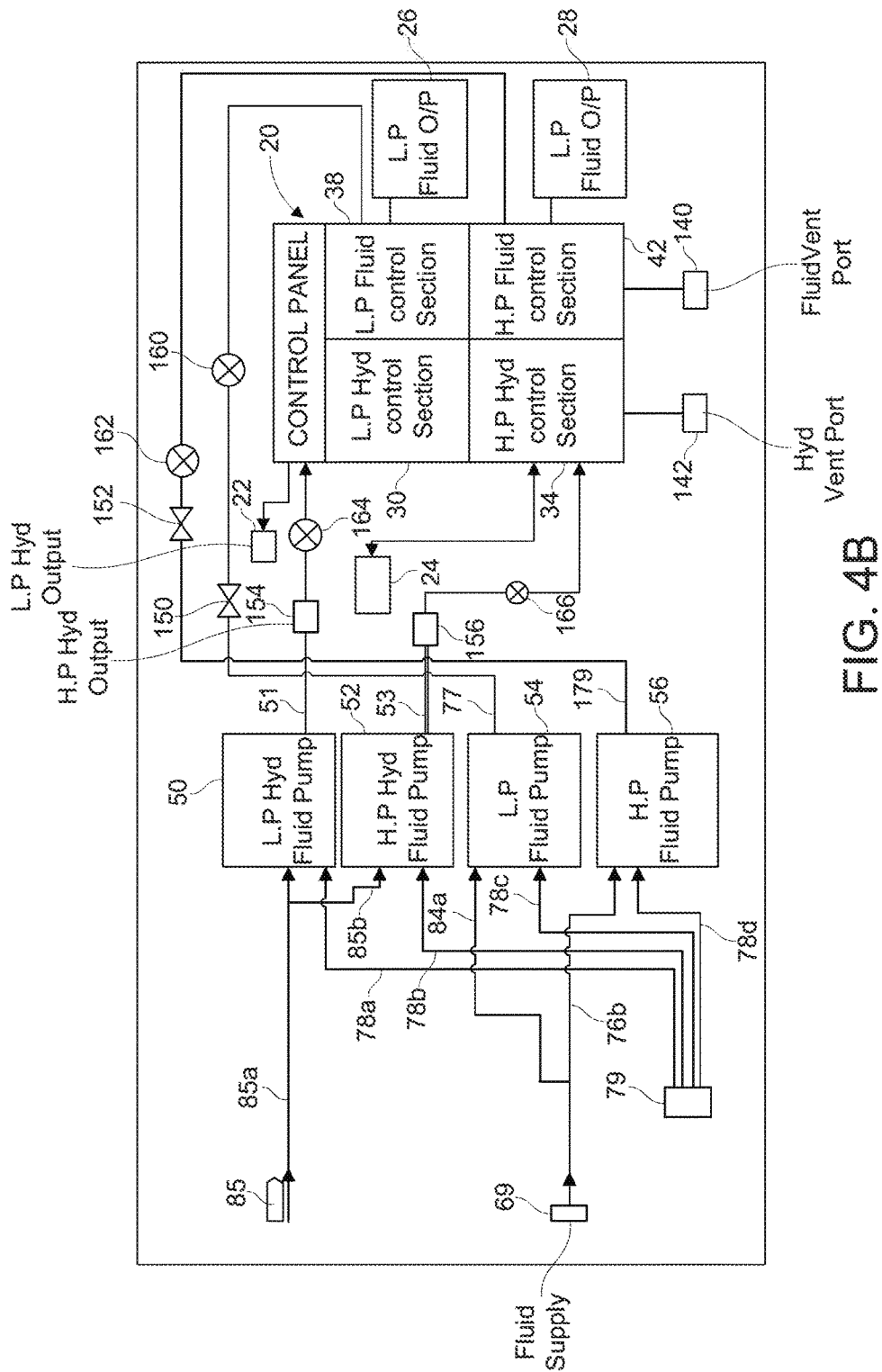

FIG. 4B shows another embodiment of the pressure testing cycle assembly 14.

The pressure testing cycle assembly 14 has a low pressure hydraulic fluid pump 50. The low pressure hydraulic fluid pump 50 can receive a low pressure air 78a from the low pressure air supply 79 and a cleaned hydraulic fluid 85a from the cleaning cycle assembly and pumping a low pressure cleaned hydraulic fluid 51.

The pressure testing cycle assembly 14 has a high pressure hydraulic fluid pump 52. The high pressure hydraulic fluid pump 52 can receive a low pressure air 78b from the low pressure air supply 79 and a cleaned hydraulic fluid 85b from the cleaning cycle assembly and pumping high pressure cleaned hydraulic fluid 53.

The pressure testing cycle assembly 14 has a low pressure fluid pump 54. The low pressure fluid pump 54 can receive a low pressure air 78c from the low pressure air supply 79 and a secondary low pressure fluid 76a from a fluid supply 69 and pumping a low pressure fluid 77.

The pressure testing cycle assembly 14 has a high pressure fluid pump 56. The high pressure fluid pump 56 can receive a low pressure air 78d from the low pressure air supply 79 and a secondary high pressure fluid 76b from the fluid supply and pumping a high pressure fluid 179.

A controller 20 connected to each of the fluid pumps for regulating pressure of the low and high pressure cleaned hydraulic fluids and the low pressure and high pressure secondary fluids to a low pressure fluid output 26 and a high pressure fluid output 28 respectively enabling pressure testing of a pressurized equipment.

The controller 20 regulates the pressure of cleaned hydraulic fluid to a low pressure hydraulic output 22 and a high pressure hydraulic output 24.

The controller has a low pressure cleaned hydraulic control section 30. The low pressure cleaned hydraulic control section 30 can compare the pressure of the low pressure air and low pressure cleaned hydraulic fluid to preset limits.

The controller 20 has a high pressure cleaned hydraulic control section 34. The high pressure cleaned hydraulic control section 34 can compare the pressure of the low pressure air and high pressure cleaned hydraulic fluid to preset limits.

The controller 20 has a low pressure secondary fluid control section 38. The low pressure secondary fluid control section 38 can compare the pressure of the low pressure air and secondary low pressure fluid to preset limits.

The controller 20 has a high pressure secondary fluid control section 42 comparing the pressure of the low pressure air and secondary high pressure fluid to preset limits.

A fluid vent port 140 can be connected to the low pressure fluid control section 38 and high pressure fluid control section 42 of the controller, and a hydraulic vent port 142 can be connected to the low pressure hydraulic control section 30 and the high pressure hydraulic control section 34 of the controller 20.

In embodiments, a plurality of fluid relief valves 150 and 152 can be mounted inline from the low pressure fluid pump 54, and the high pressure fluid pump 56 respectively, prior to the controller 20.

A plurality of burst discs 160 and 162 can be mounted in line with the fluid relief valves 150 and 152, respectively.

In embodiments, a plurality of hydraulic relief valves 154 and 156 can be mounted inline from the low pressure hydraulic fluid pump 50 and the high pressure hydraulic fluid pump 52, respectively, prior to the controller 20.

A plurality of hydraulic burst discs 164 and 166 can be mounted in line with the hydraulic relief valves 154 and 156, respectively.

In embodiments, the controller simultaneously (i) regulates the cleaning of the first and second dirty hydraulic fluids; (ii) regulates the flow of air and pressure of: high and low pressure cleaned hydraulic fluids for pressure testing of the first group of pressurized equipment, and (iii) regulates the flow of air and pressure of high and low pressure secondary fluids for pressure testing of the second group of pressurized equipment.

Figure 5:
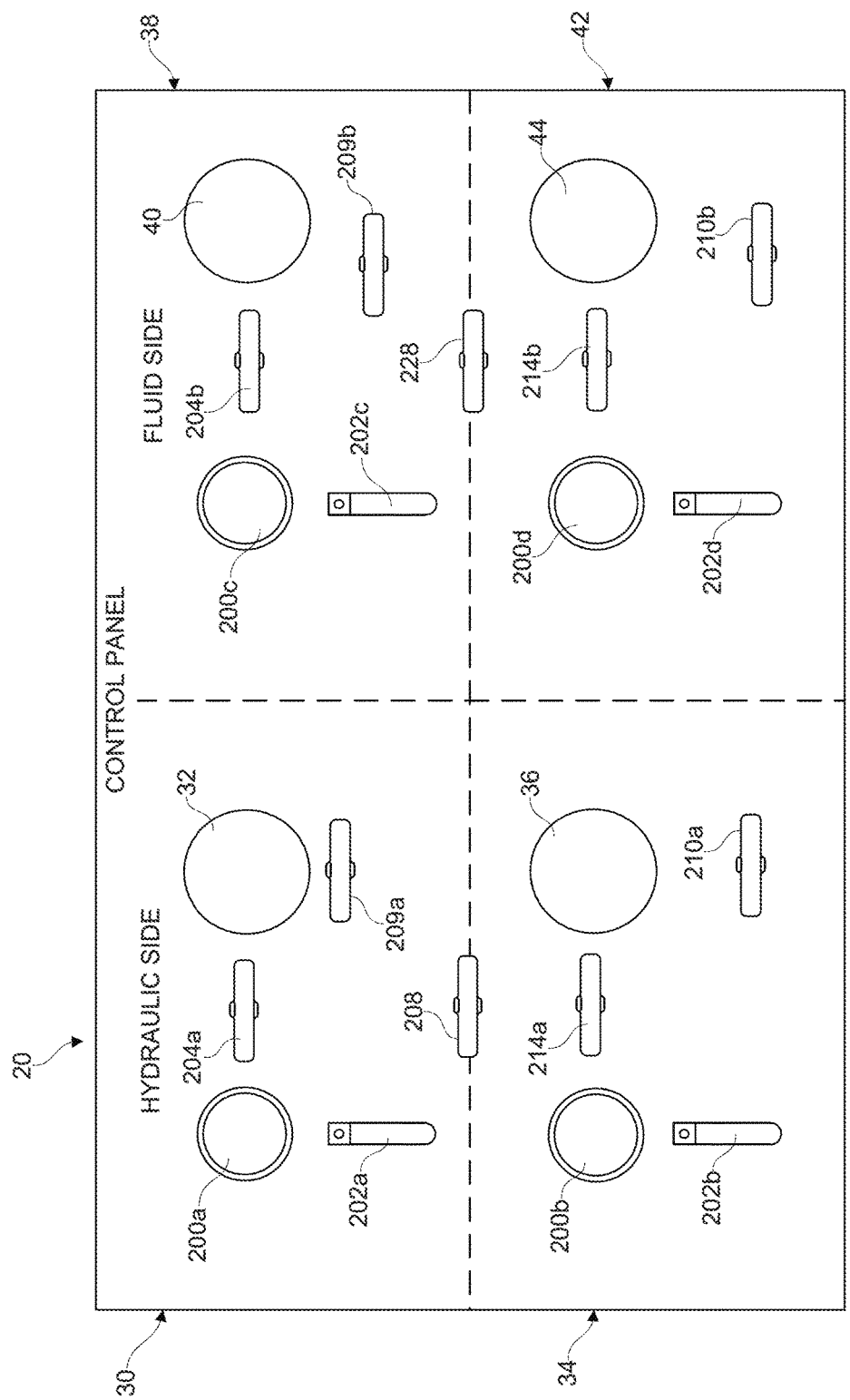
FIG. 5 depicts a controller according to an embodiment of the invention.

FIG. 5 shows an embodiment of the controller 20.

The low pressure hydraulic control section 30 has a first air regulator 200a connected to the low pressure air supply.

The low pressure hydraulic control section 30 has an air ball valve 202a fluidly connecting with the low pressure hydraulic fluid pump.

The low pressure hydraulic control section 30 has a first low pressure isolation valve 204a for controlling low pressure hydraulic flow.

The low pressure hydraulic control section 30 has a low pressure hydraulic gauge 32 measuring low pressure hydraulic fluid pressure from the low pressure hydraulic fluid pump.

The low pressures hydraulic control section 30 has a low pressure hydraulic vent 209a connected to the fluid vent port 140.

The low pressure hydraulic control section 30 has a hydraulic cross over valve 208 connecting the low pressure hydraulic control section 30 to the high pressure hydraulic control section 34.

The controller 20 has the high pressure hydraulic control section 34 containing a second air regulator 200b connected to the low pressure air supply 79.

The high pressure hydraulic control section 34 has a second air ball valve 202b fluidly connecting with the high pressure hydraulic fluid pump.

The high pressure hydraulic control section 34 has a first high pressure isolation valve 214a controlling high pressure hydraulic fluid.

The high pressure hydraulic control section 34 has a high pressure hydraulic gauge 36 measuring high pressure hydraulic fluid.

The high pressures hydraulic control section 34 has a high pressure hydraulic vent 210a connected to the hydraulic vent port 142.

FIG. 5 shows the low pressure fluid control section 38 having a third air regulator 200c connected to the low pressure air supply; a third air ball valve 202c fluidly connecting with the low pressure fluid pump; a second low pressure isolation valve 204b for controlling low pressure fluid flow; a low pressure fluid gauge 40 measuring low pressure fluid pressure from the low pressure fluid pump; and a fluid cross over valve 228 connecting the low pressure fluid control section 38 to the high pressure fluid control section 42.

The low pressure fluid control section 38 has a low pressure fluid vent 209b connected to the fluid vent port 140.

In the controller 20, the high pressure fluid control section 42 has a fourth air regulator 200d connected to the low pressure air supply; a fourth air ball valve 202d fluidly connecting with the high pressure fluid pump; a second high pressure isolation valve 214b controlling high pressure fluid; and a high pressure fluid gauge 44 measuring high pressure fluid pressure from the high pressure fluid pump. For example the high pressure fluid pressure can range from 250 psi to 22,500 psi.

The high pressure fluid control section 42 has a high pressure fluid vent 210b connected to the fluid vent port 140.

In an embodiment, the low pressure air supply transmits low pressure air from 1 psi to 160 psi.

In embodiments, the controller operates without the need for electricity and wherein the multistage filtration device can flow cleaned hydraulic fluid to at least one of: a first dirty hydraulic fluid supply and a second dirty hydraulic fluid supply.

Example One

The filtration and testing device is in a frame that is 4 feet long by 4 feet high and 4 feet deep and made from 2 inch inner diameter steel square tubing for simultaneously cleaning a "443" hydraulic fluid on an offshore oil rig and providing pressure testing for equipment located on the rig, using pressures ranging from 250 psi to 22500 psi a subsea of a Christmas tree using 443 fluid cleaned by the device. After the fluid is cleaned, 443 fluid is used by the low pressure hydraulic pump to function the Christmas tree valves. Then, the fluid side with water is used to pressure test the bore of the Christmas tree to make sure the valves seals; hence, preventing a Macondo disaster.

In this example, the cleaning cycle assembly uses a pneumatic diaphragm pump such as those made by Aero, to push the 443 glycol hydraulic fluid 60 with the air regulator such as at 5.5 gallons a minute using low pressure air at a psi around 100 psi, from a low pressure air supply located on the offshore rig.

In this example, a first dirty hydraulic fluid from a first dirty hydraulic fluid supply is cleaned to provide a first cleaned tote tank of class 6 or better hydraulic fluid. After the first tote is cleaned a second dirty hydraulic fluid from a second dirty hydraulic fluid tote can be cleaned simultaneously while pressure testing using the cleaned hydraulic fluid from the first tote.

The first and second dirty hydraulic fluids can be cleaned using a multistage filtration device with a 3 micron filter connected in series with a 1 micron filter connected in series with a 0.5 micron sock filter connected to the diaphragm pump producing cleaned hydraulic fluid.

The device includes a pressure testing cycle assembly with a controller 20 providing simultaneously: a low pressure hydraulic output from 250 to 6000 maximum psi; a high pressure hydraulic output from 6000 to 22,500 maximum psi; a low pressure fluid output 250 to 6000; and a high pressure fluid output from 6000 to 22,500 maximum psi and a crossover valve that allows low pressure fluid to enter the high pressure circuit to pressure faster and at a higher volume and a higher flow rate than the high pressure pumps can generate.

The controller has a low pressure hydraulic control section 30, a high pressure hydraulic control section 34, a low pressure fluid control section 38, a high pressure fluid control section 42.

The pressure testing cycle assembly has a first liquid strainer 70 for straining cleaned hydraulic fluid 85 forming strained cleaned hydraulic fluid 87ab and a second strainer 72 straining low pressure air 78 and a second liquid strainer 74 for straining a fluid 76 from a fluid supply 69.

Four pumps are used in two pairs. First, a low pressure hydraulic fluid pump 50 is used to receive at least one of: a strained cleaned hydraulic fluid 87ab; and a strained low pressure air 67a from the second strainer 72 for pumping low pressure cleaned hydraulic fluid 51 to the controller 20 through the low pressure hydraulic output 22.

Paired with the first pump is a second pump, a high pressure hydraulic fluid pump 52 is configured for receiving at least one of: a strained cleaned hydraulic fluid 87ab and a strained low pressure air 67b from the second strainer 72 for pumping high pressure cleaned hydraulic fluid 53 to the controller 20 through the high pressure hydraulic output 24.

The first pump of the second pair of pumps is a low pressure fluid pump 54 receiving a strained fluid 84a from the second liquid strainer 74 and a strained low pressure air 67c from the second strainer 72 for pumping the low pressure fluid 77 to the controller 20 through the low pressure fluid output 26.

The second pump of the second pair of pumps is a high pressure fluid pump 56 receiving a strained fluid 84b from the second liquid strainer 74 and strained low pressure air 67d from the second strainer 72 for pumping high pressure fluid 179 to the controller 20 through the high pressure fluid output 28.

In this example, the controller regulates the pressure of cleaned hydraulic fluid and pressure of another fluid, such as water. The controller regulates hydraulic fluid flow to a low pressure hydraulic output 22 and a high pressure hydraulic output 24. The controller regulates fluid flow, such as water flow, to a low pressure fluid output 26 and a high pressure fluid output 28. The controller regulates all four outputs simultaneously, enabling pressure testing of pressurized equipment 11 without electricity to the controller, while simultaneously cleaning hydraulic fluid or another fluid.

Example 2

A floating vessel with a length overall of 400 feet is used.

A filtration and testing device 10 is mounted to the hull of the floating vessel for simultaneously performing (a) cleaning of fluid used in oil and natural gas industry for completions, workovers, and commissionings of a wells; (b) pressure testing of a first group of pressurized equipment using fluid cleaned by the filtration and testing device, and (c) pressure testing of a second group of pressurized equipment using fluid cleaned by the filtration and testing device.

The floating vessel contains a hull that has a beam of 32 feet.

A support structure is mounted to the deck of the floating vessel. The support structure is clamped to the deck of the hull.

The support structure can be an open frame with 2 inch outer diameter square steel tubing that is hollow. The support structure can be 4 feet long by 4 feet high and 4 feet deep.

The support structure contains a cleaning cycle assembly.

The cleaning cycle assembly has a pneumatic diaphragm pump such as those made by ARO that can do 14.8 gallons per minute. The pneumatic diaphragm pump receives low pressure air at a psi ranging from 90 to 160 psi from a low pressure air supply on the vessel. In this embodiment, the air supply can be an air compressor connected to the ships system The low pressure air actuates the pump and the actuated pump pulls sequentially: a first dirty hydraulic fluid that is a glycol based fluid with particulate having a diameter of 12 microns to 20 microns from a first dirty hydraulic fluid supply on the floating vessel, which was stored in a tote tank. The same pump pulls a second dirty hydraulic fluid having the same content of particulate from a second dirty hydraulic fluid supply that is an accumulator attached to the hull. Once the first dirty hydraulic fluid is cleaned, the pump then pulls the second dirty hydraulic fluid.

The pump transfers the dirty hydraulic fluid to a multistage filtration device fluidly connected to the pump receiving the first or second dirty hydraulic fluid from the pump and producing a cleaned hydraulic fluid which can be recycled through the cleaning assembly until the fluid achieves a particulate free content desired by a user.

In this example, the multistage filtration device has one 3 micron spin on filter fluidly connected to one 1 micron spin on filter, and one 0.5 micron sock filter.

The cleaned fluid is transferred to a pressure testing cycle assembly inside the support structure.

The pressure testing cycle assembly has a low pressure hydraulic fluid pump such as a 250 to 5999 psi to receive a low pressure air at a psi of 125 while receiving a first cleaned hydraulic fluid from the multistage filtration device. The low pressure hydraulic pump at a flow rate of 3.6 gallons per minute pumps a low pressure cleaned hydraulic fluid to a low pressure section of a controller.

The pressure testing cycle assembly has a high pressure hydraulic fluid pump such as a 6000 to 22500 psi receiving a low pressure air at a psi of 125 and second cleaned hydraulic fluid from the multistage filtration device. The high pressure hydraulic pump at a flow rate of 0.25 gallons per minute pumps a high pressure cleaned hydraulic fluid to a high pressure section of the controller.

The pressure testing cycle assembly has a low pressure fluid pump, such as a 3000 to 5000 psi to receive a low pressure air at a psi of 125 while receiving a first secondary low pressure fluid which can be water for bore testing. The low pressure fluid pump can pump at a flow rate of 2.5 gallons per minute of a low pressure fluid to a low pressure section of the controller.

The pressure testing cycle assembly has a high pressure fluid pump receiving a low pressure air from the vessel at the psi of 125 and a second secondary high pressure fluid which can be water again, for bore testing. The high pressure fluid pump pumping a high pressure fluid to a high pressure fluid section of the controller.

A controller is connected to each of the fluid pumps for regulating pressure of the low and high pressure cleaned hydraulic fluid and the low pressure and high pressure secondary fluids.

The controller has a low pressure cleaned hydraulic control section 30 comparing to preset limits, such as 80 psi, the pressure of the low pressure air and low pressure cleaned hydraulic fluid will reach a pressure of 5280 psi.

The controller has a high pressure cleaned hydraulic control section 34 comparing to preset limits, such as 64 psi, the pressure of the low pressure air and high pressure cleaned hydraulic fluid will reach a pressure of 19200 psi.

The controller has a low pressure secondary fluid control section 38 comparing to preset limits, such as 34 psi, the pressure of the low pressure air and first secondary low pressure fluid (water) will reach a pressure of 2040 psi.

The controller has a high pressure secondary fluid control section 42 comparing to preset limits, such as 70 psi, the pressure of the low pressure air and second secondary high pressure fluid will reach a pressure of 21000 psi.

The controller simultaneously (i) regulates the cleaning of the first and second dirty hydraulic fluids; (ii) regulates the flow of air and pressure of high and low pressure cleaned hydraulic fluids for pressure testing of the first group of pressurized equipment 11a, (iii) regulates the flow of air and pressure of high and low pressure secondary fluids for pressure testing of the second group of pressurized equipment 11b.

Example 3

A floating vessel is workboat with a length overall of 250 feet is used.

A filtration and testing device is mounted to the hull of the floating vessel for simultaneously performing (a) cleaning of fluid used in oil and natural gas industry for completions, workovers, and commissioning of a well; (b) pressure testing of a first group of pressurized equipment using fluid cleaned by the filtration and testing device, and (c) pressure testing of a second group of pressurized equipment using fluid cleaned by the filtration and testing device.

The floating vessel a hull that has a beam of 12 feet.

A support structure is mounted to the deck of the floating vessel. The support structure has a base that is welded to the deck of the hull.

The support structure can be a perforated hinged locking sides made from ¼ inch plate steel. The support structure can be 6 feet long by 10 feet high and 4 feet deep.

The support structure contains a cleaning cycle assembly.

The cleaning cycle assembly has an electric flushing pump connected to the ship's power supply that can do 27 gallons per minute. The electric flushing pump receives amperage of 110 volts. The actuated pump pulls sequentially: a first dirty hydraulic fluid that is an OCEANIC™ 443 fluid with 10 wt % particulate having a diameter of 9 first dirty hydraulic fluid supply in a tank on the floating vessel. The same pump pulls a second dirty hydraulic fluid having the same content of particulate from a second dirty hydraulic fluid supply that is a tubing hanger sitting on the deck of the floating vessel. Once the first dirty hydraulic fluid is cleaned, the pump then pulls the second dirty hydraulic fluid for cleaning and use in testing the tubing hanger and tubing hanger running tools.

The pump transfers the dirty hydraulic fluid to a multistage filtration device fluidly connected to the pump receiving the first or second dirty hydraulic fluid from the pump and producing a cleaned hydraulic fluid which can be recycled through the cleaning assembly until the fluid achieves a particulate free content desired by a user.

In this example, the multistage filtration device has two 3 micron spin on filter fluidly connected to two 1 micron spin on filters, and no sock filter.

The cleaned fluid is transferred to a pressure testing cycle assembly inside the support structure.

The pressure testing cycle assembly has a low pressure hydraulic fluid pump such as a 4200 psi pump to receive a low pressure air at a psi of 145 while receiving a first cleaned hydraulic fluid from the multistage filtration device. The low pressure hydraulic pump at a flow rate of 4 gallons per minute pumps a low pressure cleaned hydraulic fluid to a low pressure section of a controller.

The pressure testing cycle assembly has a high pressure hydraulic fluid pump such as a 18000 psi receiving a low pressure air at a psi of 145 and second cleaned hydraulic fluid from the multistage filtration device. The high pressure hydraulic pump at a flow rate of 1.5 gallons per minute pumps a high pressure cleaned hydraulic fluid to a high pressure section of the controller.

The pressure testing cycle assembly has a low pressure fluid pump, such as a 1000 to 5000 psi to receive a low pressure air at a psi of 145 while receiving a first secondary low pressure fluid which can be a hydraulic fluid, such as TRANSAQUA™ hydraulic fluid for tubing hanger testing. The low pressure fluid pump can pump at a flow rate of 6.5 gallons per minute of a low pressure fluid to a low pressure section of the controller.

The pressure testing cycle assembly has a high pressure fluid pump receiving a low pressure air from the vessel at the psi of 145 and a second secondary high pressure fluid which can be the TRANSAQUA™ hydraulic fluid again, for tubing hanger tool testing. The high pressure fluid pump pumps a high pressure fluid to a high pressure fluid section of the controller.

A controller is connected to each of the fluid pumps for regulating pressure of the low and high pressure cleaned hydraulic fluid and the low pressure and high pressure secondary fluids.

The controller has a low pressure cleaned hydraulic control section 30 comparing to preset limits, such as 30 psi, low pressure cleaned hydraulic fluid will reach a pressure of 1800 psi.

The controller has a high pressure cleaned hydraulic control section 34 comparing to preset limits, such as 50 psi, high pressure cleaned hydraulic fluid will reach a pressure of 15000 psi.

The controller has a low pressure secondary fluid control section 38 comparing to preset limits, such as 60 psi, first secondary low pressure fluid (hydraulic fluid) will reach a pressure of 3600 psi.

The controller has a high pressure secondary fluid control section 42 comparing to preset limits, such as 40 psi, second secondary high pressure fluid, a hydraulic fluid, will reach a pressure of 12000 psi.

The controller simultaneously (i) regulates the cleaning of the first and second dirty hydraulic fluids; (ii) regulates the flow of air and pressure of high and low pressure cleaned hydraulic fluids for pressure testing of the first group of pressurized equipment 11a, (iii) regulates the flow of air and pressure of high and low pressure secondary fluids for pressure testing of the second group of pressurized equipment 11b.

While these embodiments have been described with emphasis on the embodiments, it should be understood that within the scope of the appended claims, the embodiments might be practiced other than as specifically described herein.

What is claimed is:

1. A floating vessel with a filtration and testing device for simultaneously performing (a) cleaning of fluid used in oil and natural gas industry for completions, workovers, and commissioning of wells, (b) pressure testing of a first group of pressurized equipment using fluid cleaned by the filtration and testing device, and (c) pressure testing of a second group of pressurized equipment using fluid cleaned by the filtration and testing device, the floating vessel comprising:
   a. a hull;
   b. a support structure mounted to the hull, the support structure containing:
      i. a cleaning cycle assembly comprising:
         (a) a pump receiving: low pressure air from a low pressure air supply actuating the pump and wherein the actuated pump sequentially pulls:
            (i) a first dirty hydraulic fluid from a first dirty hydraulic fluid supply; and
            (ii) a second dirty hydraulic fluid from a second dirty hydraulic fluid supply;
         (b) a multistage filtration device fluidly connected to the receiving the first or second dirty hydraulic fluid from the pump and producing a cleaned hydraulic fluid;
      ii. a pressure testing cycle assembly comprising:
         (a) a low pressure hydraulic fluid pump receiving a low pressure air from the low pressure air supply and receiving a cleaned hydraulic fluid from the cleaning cycle assembly and pumping a low pressure cleaned hydraulic fluid;
         (b) a high pressure hydraulic fluid pump receiving a low pressure air from the low pressure air supply and receiving a cleaned hydraulic fluid from the cleaning cycle assembly and pumping high pressure cleaned hydraulic fluid;
         (c) a low pressure fluid pump receiving a low pressure air from the low pressure air supply and receiving a secondary low pressure fluid from a fluid supply and pumping a low pressure fluid;

(d) a high pressure fluid pump receiving a low pressure air from the low pressure air supply and receiving a secondary high pressure fluid from the fluid supply and pumping a high pressure fluid; and iii. a controller connected to each of the fluid pumps for regulating pressure of the low and high pressure cleaned hydraulic fluids and the low pressure and high pressure secondary fluids, the controller comprising:

(a) a low pressure cleaned hydraulic control section comparing to preset limits, the pressure of the low pressure air and low pressure cleaned hydraulic fluid;

(b) a high pressure cleaned hydraulic control section comparing to preset limits, the pressure of the low pressure air and high pressure cleaned hydraulic fluid;

(c) a low pressure secondary fluid control section comparing to preset limits, the pressure of the low pressure air and secondary low pressure fluid;

(d) a high pressure secondary fluid control section comparing to preset limits, the pressure of the low pressure air and secondary high pressure fluid; and wherein the controller simultaneously (i) regulates the cleaning of the first and second dirty hydraulic fluids; (ii) regulates the flow of air and pressure of: high and low pressure cleaned hydraulic fluids for pressure testing of the first group of pressurized equipment, and (iii) regulates the flow of air and pressure of high and low pressure secondary fluids for pressure testing of the second group of pressurized equipment.

2. The floating vessel with filtration and testing device of claim 1, wherein the controller operates without electricity and wherein the multistage filtration device flows cleaned hydraulic fluid to at least one of: a first dirty hydraulic fluid supply and a second dirty hydraulic fluid supply.

3. The floating vessel with filtration and testing device of claim 1, wherein the low pressure air is strained prior to actuating each pump.

4. The floating vessel with filtration and testing device of claim 1, comprising a first liquid strainer receiving cleaned hydraulic fluid forming a strained cleaned hydraulic fluid; a second strainer straining low pressure air and forming strained low pressure air; and a second liquid strainer for straining a fluid from a fluid supply and forming strained fluid.

5. The floating vessel with filtration and testing device of claim 4, wherein the low pressure hydraulic fluid pump receives strained cleaned hydraulic fluid and the high pressure hydraulic fluid pump receives strained hydraulic fluid.

6. The floating vessel with filtration and testing device of claim 1, comprising: a first ball valve regulating flow from the fluid supply, and a first air ball valve regulating flow of the low pressure air.

7. The floating vessel with filtration and testing device of claim 1, comprising: a third ball valve regulating flow of a first dirty hydraulic fluid, a fourth ball valve regulating flow of a second dirty hydraulic fluid, and a fifth ball valve regulating flow between the first and second dirty hydraulic fluids, a sixth ball valve regulating flow of cleaned hydraulic fluid to the low pressure hydraulic fluid pump and the high pressure hydraulic fluid pump, and a seventh ball valve regulating flow of cleaned hydraulic fluid from the multistage filtration device.

8. The floating vessel with filtration and testing device of claim 1, comprising a first air filter and a second air filter connected in series for cleaning low pressure air respectively, from the low pressure air supply.

9. The floating vessel with filtration and testing device of claim 1, comprising a plurality of fluid relief valves, each fluid relief valve mounted inline from the low pressure fluid pump, and the high pressure fluid pump respectively, prior to the controller.

10. The floating vessel with filtration and testing device of claim 9, comprising a plurality of burst discs, wherein each burst disc is mounted in line with the fluid relief valves, respectively.

11. The floating vessel with filtration and testing device of claim 9, comprising a plurality of hydraulic relief valves, each hydraulic relief valve mounted inline from the low pressure hydraulic fluid pump and the high pressure hydraulic fluid pump, respectively, prior to the controller.

12. The floating vessel with filtration and testing device of claim 11, comprising a plurality of hydraulic burst discs, wherein each hydraulic burst discs is mounted in line with the hydraulic relief valves, respectively.

13. The floating vessel with filtration and testing device of claim 1, wherein the low pressure air supply transmits low pressure air at a pressure from 1 psi to 160 psi.

14. The floating vessel with filtration and testing device of claim 1, wherein the multistage filtration device comprises:

a. a 1 to 3 micron spin on filter receiving the first or second dirty hydraulic fluid and forming slightly cleaned hydraulic fluid;

b. a 0.5 to 3 micron spin on filter fluidly connected to the 1 to 3 micron spin on filter forming a partially cleaned hydraulic fluid from the slightly cleaned hydraulic fluid;

c. 0.5 to 10 micron sock filter fluidly connected to the 0.5 to 3 micron filter forming the cleaned hydraulic fluid from the partially cleaned hydraulic fluid; and d. a sample port connected to a tubing from the pump enabling authentication of filtration of the hydraulic fluid.

15. The floating vessel with filtration and testing device of claim 1 comprising: a fluid vent port connected to the low pressure fluid control section and high pressure fluid control section of the controller; and a hydraulic vent port connected to the low pressure hydraulic control section and the high pressure hydraulic control section of the controller.

16. The floating vessel with filtration and testing device of claim 1, comprising a stand-alone 0.5 to 10 micron sock filter for receiving at least one return fluid from each group of pressurized equipment.

17. The floating vessel with filtration and testing device of claim 1, wherein the low pressure hydraulic control section comprises:

a. a first air regulator connected to the low pressure air supply;

b. a first air ball valve controlling flow of low pressurize air to the low pressure hydraulic fluid pump;

c. a first low pressure isolation valve controlling flow of low pressure hydraulic fluid;

d. a low pressure hydraulic gauge measuring low pressure hydraulic fluid flowing from the low pressure hydraulic fluid pump;

e. a low pressure hydraulic vent connected to a hydraulic vent port; and f. a hydraulic cross over valve connecting the low pressure hydraulic control section to the high pressure hydraulic control section.

18. The floating vessel with filtration and testing device of claim 17, wherein the high pressure hydraulic control section comprises:
  a. a second air regulator connected to the low pressure air supply;
  b. a second air ball valve fluidly controlling flow of low pressurize air to the high pressure hydraulic fluid pump;
  c. a first high pressure isolation valve controlling flow of high pressure hydraulic fluid;
  d. a high pressure hydraulic gauge measuring high pressure hydraulic fluid flowing from the high pressure hydraulic fluid pump; and
  e. a high pressure hydraulic vent connected to a hydraulic vent port.

19. The floating vessel with filtration and testing device of claim 18, wherein the low pressure fluid control section comprises:
  a. a third air regulator connected to the low pressure air supply;
  b. a third air ball valve controlling flow of low pressurize air to the low pressure fluid pump;
  c. a second low pressure isolation valve controlling flow of low pressure fluid;
  d. a low pressure fluid gauge measuring low pressure fluid flowing from the low pressure fluid pump;
  e. a low pressure fluid vent connected to a fluid vent port; and
  f. a fluid cross over valve connecting the low pressure fluid control section to the high pressure fluid control section.

20. The floating vessel with filtration and testing device of claim 19, wherein the high pressure fluid control section comprises:
  a. a fourth air regulator connected to the low pressure air supply;
  b. a fourth air ball valve controlling flow of low pressurize air to the high pressure fluid pump;
  c. a second high pressure isolation valve controlling flow of high pressure fluid;
  d. a high pressure fluid gauge measuring high pressure fluid flowing from the high pressure fluid pump; and
  e. a high pressure fluid vent connected to a fluid vent port.

* * * * *